(12) United States Patent
Imbert et al.

(10) Patent No.: US 9,234,131 B2
(45) Date of Patent: Jan. 12, 2016

(54) USE OF LANTHANIDE COMPLEXES FOR OPTICAL MARKING OF PRODUCTS

(71) Applicant: COMMISSARIAT A L'ENERGIE ATOMIQUE ET AUX ENERGIES ALTERNATIVES, Paris (FR)

(72) Inventors: Daniel Imbert, Vouray (FR); Marinella Mazzanti, Saint Martin le Vinous (FR); Nicolas Wartenberg, Grenoble (FR); Olivier Raccurt, Chelieu (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 165 days.

(21) Appl. No.: 13/936,349

(22) Filed: Jul. 8, 2013

(65) Prior Publication Data
US 2014/0008576 A1 Jan. 9, 2014

(30) Foreign Application Priority Data
Jul. 9, 2012 (FR) ...................................... 12 56609

(51) Int. Cl.
C09K 11/06 (2006.01)
C07F 5/00 (2006.01)
C09K 11/77 (2006.01)
B42D 25/382 (2014.01)
B42D 25/387 (2014.01)

(52) U.S. Cl.
CPC .............. *C09K 11/06* (2013.01); *B42D 25/382* (2014.10); *B42D 25/387* (2014.10); *C07F 5/00* (2013.01); *C09K 11/77* (2013.01); *C09K 2211/1074* (2013.01); *C09K 2211/182* (2013.01)

(58) Field of Classification Search
CPC .... C09K 11/06; C09K 2211/182; C09D 5/22; C07F 5/00; B42D 25/36
USPC ...................... 252/301.16, 301.34; 106/31.32; 427/157; 428/690; 534/15; 250/459.1, 250/473.1
See application file for complete search history.

(56) References Cited

U.S. PATENT DOCUMENTS

| | | | |
|---|---|---|---|
| 7,077,329 B2 * | 7/2006 | Chang et al. .................. 235/491 |
| 2006/0163492 A1 * | 7/2006 | Mennicken et al. ........ 250/483.1 |
| 2009/0042314 A1 | 2/2009 | Capobianco et al. |
| 2010/0072424 A1 | 3/2010 | Petoud et al. |
| 2010/0108961 A1 | 5/2010 | Guillou et al. |
| 2011/0018252 A1 | 1/2011 | Petry et al. |
| 2011/0112289 A1 * | 5/2011 | Giraud et al. .................. 540/465 |

FOREIGN PATENT DOCUMENTS

| | | |
|---|---|---|
| EP | 1873588 A2 | 1/2008 |
| WO | 2004101708 A1 | 11/2004 |
| WO | 2008012225 A1 | 1/2008 |
| WO | 2009037277 A1 | 3/2009 |
| WO | WO 2009/037277 * | 3/2009 |

OTHER PUBLICATIONS

Andreiadis et al, "Self-assembly of highly luminescent lanthanide complexes promoted by pyridine-tetrazolate ligands", Dalton Transactions, 2012, 41, pp. 1268-1277, Nov. 29, 2011.*
Wartenberg et al, "Luminescent latex particles loaded with anionic lanthanide complexes: a versatile platform for multicolor optical coding", Journal of Material Chemistry C, 2013, 1, 2061-2063, Jan. 24, 2013.*
Wartenberg et al, "Multicolour Optical Coding from a Series of Luminescent Lanthanide Complexes with a Unique Antenna", Chem. Eur. J. 2013, 19, 3477-3482, Jan. 25, 2013.*
Andreiadis et al., "Self-assembly of highly luminescent lanthanide complexes promoted by pyridine-tetrazolate ligands", Dalton Transactions, 2012, vol. 41, pp. 1268-1277.
Andrews et al., "Synthesis and structural characterisation of cationic neutral and hydroxo-bridged lanthanoid (La, Gd, Ho, Yb, Y) bis 5-(2-pyridyl)tetrazolate complexes", Polyhedron, 2007, vol. 26, pp. 5406-5413.
Duati et al., "Enhancement of Luminescense Lifetimes of Mononuclear Ruthenium(II)-Terpyridine Complexes by Manipulation of the .sigma.-Donor Strength of Ligands", Inorganic Chemistry, 2003, vol. 42, No. 25, pp. 8377-8384, XP002486394.
Bunzli et al., "Taking advantage of luminescent lanthanide ions", Chemical Society Reviews, 2005, vol. 34, pp. 1048-1077.
French Search Report, dated Sep. 26, 2012, from corresponding EP application.

* cited by examiner

Primary Examiner — Carol M Koslow
(74) Attorney, Agent, or Firm — Young & Thompson

(57) ABSTRACT

A method of optical marking of products by either applying a composition including at least one lanthanide complex and a vehicle on at least part of a surface or a product, or incorporating a composition including at least one lanthanide complex and a vehicle into at least part of a product. The lanthanide complex is according to Formula I: $[Ln(L)_3]^{3-} \cdot (Cat)_3$, wherein: Ln is a lanthanide, Cat is a cation and L is a ligand of formula II:

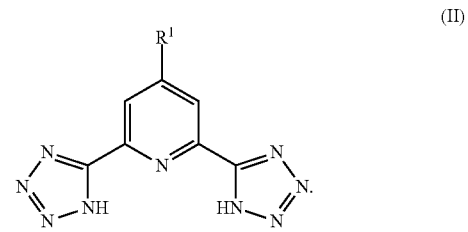

(II)

7 Claims, 5 Drawing Sheets

USE OF LANTHANIDE COMPLEXES FOR OPTICAL MARKING OF PRODUCTS

This invention relates to the use of at least one lanthanide complex for optical marking of products, compositions for optical marking of products, an optical marking method including an application step of these compositions, and lanthanide complexes used in these compositions.

Optical marking of products for the purpose of the invention means the addition of at least one chemical substance that can be identified by the emission of a signal or a specific optical spectrum after irradiation at one or several particular wavelength(s), to said products. Non-limitative examples of optical marking include securing and authentication of documents and particularly passports and bank notes, products of all types and particularly electronic, computer products, packaging of pharmaceutical products, and luxury articles such as handbags.

Securing and authentication of all types of documents and products have become more and more necessary after many observed acts of forgery and counterfeit. Some products or official documents are frequently marked by one or several very specific distinctive signs in an attempt to reduce and prevent these offenses. Obviously, it must be very difficult for anyone to reproduce such markings, while it must also be easy to verify them by easy-to-use identification methods.

One technique for marking products and documents is optical marking using a material or substance that can be identified by the emission of a specific signal or optical spectrum after irradiation at one or several particular wavelength(s). These markers are usually invisible to the naked eye under traditional ambient light. Some may emit a particular colour that becomes visible to the naked eye under irradiation by ultraviolet (UV) or infrared (IR) light. However, this does not necessarily provide sufficient security because such markers are often easily identifiable and reproducible. The use of optical markers with complex and specific emission spectra that can be detected and measured by means of a measurement instrument such as a fluorimeter or a spectrophotometer gives a much higher level of security. Some enterprises, certified dealers or institutions such as customs, police or other national authorities use such markings as inspection means to verify the authenticity of a product or a document.

Markers based on organic fluorophores are examples of optical markers with several colour codes. For example, patent application WO2004/101708 discloses the use of polymeric materials containing luminescent pigments such as rhodamine. Each colour is obtained by means of a specific compound that emits a light signal at an excitation wavelength specific to said pigment. Therefore, several different organic molecules have to be associated if a multi-colour optical code is to be obtained, which has the disadvantage that they cannot be identified at the same excitation wavelength. Furthermore, such compounds are usually not stable to photochemical bleaching and sometimes cannot be discriminated from the chromophoric components intrinsic to the materials containing them.

Apart from organic chromophoric compounds, lanthanides are particularly attractive for optical marking applications because they have a very thin emission band at fixed wavelengths (making the emitted colour very pure) that are not affected by environmental factors such as the pH or temperature. Furthermore, this signal is very easily detected and discriminated from the background noise of the materials wherein they are contained. Furthermore, the life of excited states of lanthanides and consequently the emitted luminescence is particularly long. Furthermore, photoluminescence quantum yields may be very high and facilitate the detection of emitted signals. Emission ranges may also be adapted and lanthanide complexes emitting in the ultraviolet (UV), visible and near infrared (NIR) spectrum ranges can be obtained.

Patent application WO2008/012225 discloses the use of mineral pigments based on lanthanides that emit light under UV irradiation. This patent application discloses two different pigments emitting in two different colour ranges to provide security against counterfeit. Furthermore, patent application US2011/0018252 discloses security pigments incorporated into transparent mineral matrices based on silica. Finally, patent application US2009/0042314 discloses the use of lanthanides incorporated into $NaYF_4$ type mineral matrices and the use of these matrices.

Excitation at low energy is impossible in this case since the antenna effect is not used, and does not provide a viable and easy-to-use optical marking method. The absorption coefficient of lanthanides is very low and their direct excitation requires the use of high energy laser sources to overcome a very limited luminescence intensity. Emission of lanthanide ion has to be sensitised by complexing it with an adapted organic chromophore capable of absorbing photons and transferring them efficiently to lanthanide ions (antenna effect), to excite emission of the metal with lower energies.

There are many different types of ligands capable of sensitising lanthanide ions (Bunzli, *Chem. Soc. Rev* 2005, 34, 1048). Nevertheless, these compounds are often not stable under hydrolysis thus leading to dissociation of the complex, or sometimes do not have a sufficient antenna effect to sensitive several lanthanides with good luminescence quantum yields. The chemical structure and synthesis of these ligands are sometimes complex and they can suffer from poor solubility in a liquid and/or solid organic medium.

Lanthanide complexes have been used for the production of coordination polymers or Metal Organic Frameworks (MOF) as disclosed in patent applications US2010/0108961 and US2010/0072424. These codes are based on compounds of different lanthanide ions that crystallise in the form of coordination polymers or infinite three-dimensional frameworks. In these compounds, each colour code requires a specific preparation. Furthermore, coordination polymers and MOFs are highly insoluble and consequently there are few possibilities for formulation of these systems.

As discussed in the examples mentioned above, an optical marker must be easy-to-use in that it can be easily formulated and is therefore soluble in organic media, and it must be identifiable by irradiation at a single wavelength using a low energy light source. It must emit complex optical signals that are difficult to reproduce but easy to read using spectrometer type standard instruments. The optical marker must be easily synthesised, resistant to photochemical bleaching and it must have good photoluminescence quantum yields. Finally, the composition of these markers must be variable depending on the user's needs, particularly concerning the diversity of colour codes provided to the user and their complexity. Such criteria are demanding and are not all satisfied concomitantly by optical markers used in prior art.

Thus, the Applicant showed initiative in developing lanthanide complexes and identifying them as optical markers that satisfy all the requirements mentioned above.

Therefore one purpose of this invention concerns the use of at least one lanthanide complex for optical marking of products, the lanthanide complex(es) being selected from compounds of formula I $$[Ln(L)_3]^{3-}.(Cat) \qquad (I)$$

wherein:

Ln is a lanthanide;

Cat is a cation used to balance the charge of the complex and is selected from $Na^+$, $K^+$, $Li^+$, $Cr^{3+}$, $Fe^{3+}$, $Fe^{2+}$, $Co^{2+}$, $Cu^{2+}$, $Mo^{6+}$, $Ru^{4+}$, $Ir^{4+}$, $Pt^{4+}$, $^+NHR^aR^bR^c$ wherein $R^a$, $R^b$ and $R^c$ may be identical or different and are independently from one another, $C_2$ to $C_{15}$ alkyl optionally substituted by one or more substituents selected from $C_2$ to $C_3$ alkenyl, aryl and heteroaryl, and $^+PR^dR^eR^fR^g$ wherein $R^d$, $R^e$ $R^f$ and $R^g$ may be identical or different and are independently selected from $C_1$ to $C_5$ alkyl and phenyl;

L is a ligand with formula II:

wherein, $R^1$ is selected from a hydrogen atom, wherein $R^2$ is $C_1$ to $C_3$ alkyl;

$R^3$ is a hydrogen atom or $C_1$ to $C_3$ alkyl;

$Ar^1$ is a 5- or 6-membered phenyl or heteroaryl; and the dashed lines indicate the point of attachment to the pyridine ring.

Lanthanides as used in the invention are the series of chemical elements from Cerium (Z=58) to Lutecium (Z=71) as defined according to the rules issued by the International Union of Pure and Applied Chemistry (IUPAC). Therefore, Ln is selected from lanthanum, cerium, praseodymium, neodymium, promethium, samarium, europium, gadolinium, terbium, dysprosium, holmium, erbium, thulium, ytterbium and lutecium.

The term "alkyl" within the meaning of the invention denotes a hydrocarbonated group with formula $C_nH_{2n-1}$ wherein n is an integer number greater than or equal to 1. Alkyl groups may be linear or branched. Examples of alkyl groups are methyl, ethyl, n-propyl, i-propyl, n-butyl, i-butyl, s-butyl, t-butyl, n-octyl ($C_8$ linear), n-decyl (linear in $C_{10}$).

The term "alkenyl" according to the invention denotes a linear or ramified unsaturated hydrocarbonate group, comprising one or several carbon-carbon double bond(s). Preferably, alkenyl groups are selected from $C_2$-$C_3$ alkenyl, and in particular vinyl and allyl.

The term "aryl" within the meaning of the invention refers to a monocyclic poly-unsaturated and/or aromatic hydrocarbon group. For example, a preferred 5-membered aryl group is 1,3-cyclopentadiene. A 6-membered aryl is for example and preferably phenyl.

The term "heteroaryl" within the meaning of the invention denotes an aromatic ring wherein, when possible depending on the valency, one or more ring atoms are replaced by an oxygen, nitrogen and/or sulphur atom or an —NH—, said nitrogen and sulphur atoms optionally being oxidised and the nitrogen atom optionally being quaternarised. Examples of heteroaryl groups include furanyl, thiophenyl, pyrazolyl, imidazolyl, oxazolyl, isoxazolyl, thiazolyl, isothiazolyl, 1,2,3-triazolyl, 1,2,4-triazolyl, 1,2,3-oxadiazolyl, 1,2,4-oxadiazolyl, 1,2,3-thiadiazolyl, 1,2,4-thiadiazolyl, tetrazolyl, oxatriazolyl, thiatriazolyl, pyridinyl, pyrimidinyl, pyrazinyl, pyridazinyl, oxazinyl, dioxinyl, thiazinyl, triazinyl, among which thiophenyl, triazolyl, oxazolyl and tetrazolyl are preferred.

Lanthanide complexes of Formula I, some of which are disclosed in patent application WO2009/037277 and in *Dalton. Trans.* 2012, 41, 1268 both in the name of the Applicant, are characterised by a high photoluminescence quantum yield and easy synthetic access. They are soluble in solid organic media such as polymers and liquids such as organic solvents while remaining stable under hydrolysis, and they are not affected by photochemical bleaching.

Lanthanide complexes of Formula I are also remarkable in that for a given cation and a given ligand but regardless of the lanthanide, they can all be excited by irradiation at a single wavelength. In other words, compounds of Formula I wherein the L and $^+$Cat groups are identical but differ from each other only by the lanthanide Ln, can be excited using a single light source, in other words at the same wavelength particularly in the UV range and preferably between 280 and 350 nm to excite all complexes according to the invention, and emit different optical signals in the UV, visible and/or near infrared (NIR) ranges.

Luminescence transitions are particular to each lanthanide ion. These transitions are thin and do not change with time either in solution or in the solid state. The antenna effect is preserved for all complexes that are excited between 290 and 330 nm. Quantum yields of complexes according to the invention are very high and are among the highest in the visible ever reported in the literature for Europium, Samarium, Dysprosium and Terbium (E. G. Moore et al., *J. Am. Chem. Soc.*, 2006, 128, 10648-10649; A. Nonat et al., *Chem. Eur. J.*, 2006, 12, 7133-7150; A. de Bettencourt-Dias, *J. Am. Chem. Soc.*, 2007, 129, 15436-15437; A. Nonat et al. *Inorg. Chem.*, 2009, 48, 4207-4218; D. Imbert et al. *Chem. Commun.*, 2005, 1432-1434; E. Brunet et al., *Photochem. Photobiolol. Sci.*, 2002, 1, 613-618.).

A mix of complexes according to the invention can give an optical code emitting in the visible for Europium, Samarium, Dysprosium and Terbium. The same applies for Praseodymium, Holmium and Thulium in the visible, or Neodymium, Ytterbium, Holmium and Praseodymium in the infrared. Quantum yields are different depending on the lanthanide used but may be grouped into three categories, namely (1) Tb, Eu, Sm and Dy that are strongly luminescent in the visible (1.5-70%), (2) Pr, Ho and Tm that are less luminescent in the visible (0.01-0.06%), and (3) Nd and Yb that are strongly luminescent in the near infrared (0.21-0.37%). Lanthanides belonging to the same category may easily be associated in coherent concentration ratios. But it is also possibly to mix the categories to increase the complexity of the code using much higher concentration ratios.

Therefore, in one particularly advantageously embodiment, at least two lanthanide complexes of Formula I will be used wherein the L and $^+$Cat groups are identical for each complex that differ from each other only by the lanthanide Ln. Therefore, it is possible to obtain very sophisticated colour codes, i.e. emission spectra, with a mix of chemical molecules with very similar structures. Therefore one major advantage of this invention is that it does not require the synthesis of several chromophoric molecules with different chemical structures that cannot even be excited at the same wavelength.

Thus, this invention provides an easy means of creating many optical codes as a result of the number of possible combinations between lanthanides Ln and ligands L that are also variable depending on the quantities of each of the complexes, the excitation wavelength and emission intensities. Emission intensities can also be easily adjustable by those skilled in the art, taking account of the luminescence quantum yield of each complex and the intensity of the signals that they emit.

The use of a mix of at least two lanthanide complexes wherein the L and $^+$Cat groups are identical is also advantageous in that the complexes have different lifetimes in the excited state. The emission spectrum of such mix compositions varies in time and it may be monitored by resolved time spectrometry. This offers an additional means of variation for the production of complex optical codes that are very difficult to reproduce, falsify or forge and to increase the diversity of possible optical codes.

A large diversity of colour codes, i.e. emission spectra, can give a colour code that can be easily discriminated from emission spectrum intrinsic to any components of the marked material and/or equipment.

Advantageously, the lanthanide Ln is selected from praseodymium, neodymium, samarium, europium, terbium, dysprosium, holmium, thulium and ytterbium Advantageously, the ligand L is such that the group $R^1$ is selected from a hydrogen atom, -continued wherein

$R^2$ is methyl or ethyl, and preferably methyl;

$R^3$ is a hydrogen atom, methyl or ethyl, and preferably a hydrogen atom or methyl; and

$Ar^1$ is phenyl or a thiophen-2-yl;

and the dashed lines indicate the point of attachment to the pyridine ring,

$R^1$ is preferably selected from a hydrogen atom, $R^1$ is more preferably selected from a hydrogen atom, -continued even more preferably $R^1$ is selected from a hydrogen atom, and most preferably, $R^1$ is a hydrogen atom.

Advantageously, the $^+$Cat cation is a cation selected from Na$^+$, K+, Li$^+$, Cr$^{3+}$, Ru$^{4+}$, Ir$^{4+}$, Pt$^4$, $^+$NHR$^a$R$^b$R$^c$ wherein R$^a$, R$^b$ and R$^c$ are identical or different and, independently from one another, are $C_2$ to $C_{15}$ alkyl, and $^+$PR$^d$R$^e$R$^f$R$^g$ wherein R$^a$, R$^b$, R$^c$ and R$^g$ are identical or different but preferably identical, are independently selected from $C_1$ to $C_5$ alkyl and phenyl, preferably R$^d$, R$^e$, R$^f$ and R$^g$ are identical and phenyl.

More advantageously, the $^+$Cat cation is selected from $^+$NHR$^a$R$^b$R$^c$ wherein R$^a$, R$^b$ and R$^c$ are identical or different and are linear or branched alkyl, preferably linear $C_1$ to $C_{12}$, and preferably in $C_1$ to $C_{10}$ alkyl, preferably R$^a$ and R$^b$ are methyl and R$^c$ is n-decyl, or R$^a$, R$^b$ and R$^c$ are identical and ethyl or n-octyl. Advantageously, the $^+$Cat cation is $^+$NHR$^a$R$^b$R$^c$ wherein R$^a$, R$^b$ and R$^c$ are identical. In this case, all three are preferably selected from ethyl and n-octyl.

In one embodiment, at least two lanthanide complexes are selected from compounds with Formula III $$[Ln(L)_3)]^3 \cdot (^+NHR^aR^bR^c)_3 \qquad (III),$$

wherein:

Ln is selected from praseodymium, neodymium, samarium, europium, terbium, dysprosium, holmium, thulium ytterbium, and preferably samarium, dysprosium, terbium and europium;

R$^a$, R$^b$ and R$^c$ are identical and are selected from ethyl and n-octyl, preferably n-octyl, or R$^a$ and R$^b$ are methyl and R$^c$ is n-decyl, preferably R$^a$, R$^b$ and R$^c$ are n-octyl L is the ligand of Formula II wherein Fe is a hydrogen atom, in other words the compound of Formula IV:

(IV)

It is particularly advantageous if at least two lanthanide complexes of Formula III are used wherein the R$^a$, R$^b$ and R$^c$ groups in each complex are identical and all three are preferably selected from ethyl and n-octyl.

More advantageously, the four lanthanide complexes of Formulae V, VI, VII and VIII are used (V);

(VI);

(VII);

(VIII);

wherein
$R^a$, $R^b$ and $R^c$ are selected from ethyl and n-octyl, and preferably n-octyl; L is the ligand of Formula II wherein $R^1$ is a hydrogen atom, in other words the compound of Formula IV.

In one embodiment, the lanthanide complexes according to the invention are not visible to the naked eye. They only emit light by irradiation at a specific wavelength in the UV, visible and NIR ranges, preferably between 250 and 370 nm, more preferably between 280 and 350 nm, and even more preferably between 310 and 330 nm. The light emitted is analysed by a spectrometer, and particularly a fluorimeter that may be simple or more sophisticated depending on the lanthanides used. For colour codes that use lanthanides emitting in the visible, a single framework low resolution fluorimeter or spectrometer may be used (detection by photodiode, photomultiplier tube). For colour codes using lanthanides emitting in the near infrared, low or medium resolution spectrometers or fluorimeters with single or double frameworks, or an imager may be used (detection by photodiode, photomultiplier tube over a range varying from 800 to 1700 nm). In the case of colour codes calling upon lanthanides with different emission lifetimes, a resolved time spectrometer should be used to detect the entire code. If the possibility of resolving the colour code in time is used, a spectrometer must be used to measure lifetimes on the nanosecond and millisecond range.

Therefore, in order to build an optical code, the emission zone of the required complex (UV, visible and/or NIR) should be taken into account to determine the choice of ligands and lanthanides. In the case of optical codes with several complexes, the quantities of each complex are to be adjusted as a function of 1) the luminescence quantum yield and 2) the relative intensity of the emitted signals. In one embodiment, stock solutions of lanthanide complexes with the same concentration are used and the colour code is prepared adjusting the volumes of each stock solution used in the mix. These adjustments as a function of the quantum yield and the luminescence intensity can optimise the read window of emitted signals so as to detect them entirely.

Another object of this invention concerns an optical product marking composition, said composition comprising at least one lanthanide complex as defined above, and a vehicle. Said vehicle is selected from solvents and polymers.

All clarifications made above relative to the use of complexes and their constitution are also applicable to compositions according to the invention.

In one embodiment, the composition according to the invention is in the form of an oil or a solution and the vehicle is chosen from the group consisting of water, organic solvents and mixtures thereof. Organic solvents for example include linear or branched $C_1$ to $C_4$ alcohols, particularly methanol, ethanol, n-propanol, iso-propanol, n-butanol, iso-butanol, tert-butanol, acetone, 2-butanone, N,N-dimethylacetamide, N,N-dimethylformamide, dimethylsulfoxide, 1,4-dioxane, tetrahydrofurane, ethyl acetate, dichloromethane, chloroform, 1,2-dichloroethane, benzene, toluene, diethyl ether, ethylene glycol, propylene glycol, diethylene glycol, dipropylene glycol, acetonitrile, N-methylpyrrolidinone. Advantageously, the vehicle is a chlorinated solvent and/or a linear or branched in $C_1$ to $C_4$ alcohol type solvent, preferably dichloromethane, chloroform, 1,2-dichloroethane, methanol, ethanol, n-propanol, iso-propanol, n-butanol, iso-butanol, tert-butanol, more preferably dichloromethane, methanol, and ethanol, and even more preferably methanol and dichloromethane.

In another embodiment, the composition according to the invention is in the form of a solid, the vehicle is then selected from polymers, preferably organic polymers. Organic polymers preferably include silicons (Si), polyesters (PE), polyacrylates and more particularly polymethylmethacrylates (PMMA), polycarbonates (PC), saturated or unsaturated polyesters, polystyrenes (PS), polypropylenes (PP), polyamides (PA), polyanilines (Pani), acrylonitriles, polyvinyl chlorides (PVC, PVC-C, PVA). Lanthanide complexes according to the invention are particularly suitable as additives in aromatic polyester type organic polymers, as for example those formed from terephthalic acids and glycols, particularly polyethyleneterephthalate (PET), PMMA, the PP or the PS.

Alternately, the vehicle is selected from the group consisting of gums, latexes and mineral powders, preferably based on metallic oxides.

Formulation possibilities may be adjusted particularly by the choice of the $^+$Cat counter-ion. The base containing this cation used to deprotonate the ligand and the cation to balance the charge of the complex may easily be changed during synthesis of the complex. The base may be the final cation in the case of tertiary amines that, after deprotonation of the ligand, produce quaternary ammonium ions. Finally, vinyl or allyl type $R^a$, $R^b R^c$ groups in $(^+NHR^a R^b R^c)_3$ may be associated with polymerisation precursors during synthesis of polymers. Alkaline metal ($Na^+$, $K^+$, $Li^+$) cations will be preferred in the case of formulations in an aqueous solution or mineral medium, while quaternary ammonium type cations will be preferred in organic solvent or organic polymer type formulations.

The invention also relates to a method of optical marking of products comprising an application step of a composition like that described above on at least part of a surface of a product or incorporation into the substance of at least part of a product.

In other words, said composition may be contained in one or several materials forming said product or may be applied on said product by a temporary or permanent attachment or bonding means, and preferably permanent.

The method according to the invention may be used particularly in the attempt to reduce counterfeit and/or to increase security or authentication of documents. The effort to reduce counterfeit includes efforts to prevent the production of non-original products such as medicines, computer products, packaging, and particularly pharmaceutical products. Therefore compositions according to the invention may be incorporated in a label or an adhesive tape, packaging material, a film of polymer material such as those listed above, an organic or inorganic glue. Fibres or security films are put into legal or certified documents in order to authenticate them or to protect them against reproduction, imitation or falsification, in other words to make them secure. Such documents include for example official papers, bank notes, cheques, tickets to shows, diplomas, identity papers, passports, payment cards, access cards, reduction forms. The compositions according to the invention may be applied by colouring or printing, particularly on paper, cardboard, wood, cellulose or even cotton fibres; they may thus be used in inks or glues. They can be applied on textile fibres in order to authenticate a product derived from the textile industry.

Therefore products that can be marked by the method according to the invention include, without limitation, medicines, computer products, packaging, particularly pharmaceutical products, labels, adhesive tapes, packaging materials, films of polymer materials like those listed above, organic or inorganic glues, fibres or security films, official papers, bank notes, cheques, show tickets, diplomas, identity papers, passports, payment cards, access cards, reduction forms, paper, cardboard, wood, cellulose or cotton fibres, inks and textile fibres.

Another purpose of the invention concerns lanthanide complexes with Formula IX wherein, Ln is selected from Yb, Nd, Ho, Pr, Tm, Sm, Dy and Tb; and
L is a ligand of Formula II wherein $R^1$ is a hydrogen atom, in other words the compound with formula IV:

The following abbreviations are used in this application: ° C.: degree(s) Celsius; calc.: calculated(s); cm: centimetre(s); δ: chemical NMR displacements expressed in ppm; D: deuterium/deuterated; DMF: N,N-dimethylformamide; eq: equivalent(s); Et: ethyl; exp.: Experimental; g: gram(s); h: hour(s); H$_2$pytz: compound of Formula IV; HPLC: High Performance Liquid Chromatography; IPA: isopropanol; IR: infrared; L: litre(s); M: mol/L; mM: mmol/L; μM: μmol/L; Me: methyl; mg: milligram(s); min: minute(s); mm: millimetre(s); ms: millisecond(s), mL: millilitre(s); mol: mole(s); mmol: millimole(s); μmol: micromole(s); MS: mass spectrometer; Oct: n-octyl; ppm: parts per million, NMR: Nuclear Magnetic Resonance, TA: ambient temperature (ca. 15-25° C.).

EXAMPLES

Lanthanide triflate salts were purchased at Aldrich and their metal content was measured before use with EDTA in the presence of xylene orange. The $^1$H and $^{13}$C NMR spectra were recorded at 298 K on a Bruker Advance 200 instrument and/or on a Varian Unity 400 instrument. Chemical displacements are shown in ppm and are referenced relative to the signals of the residual solvent. The mass spectra were produced on a Thermo Scientific LXQ spectrometer equipped with an "electrospray" ionisation source. Elementary analyses were made by the CNRS Central Analysis Service (Vernaison, France).

The absorption spectra were produced in a 1 cm quartz cell on a Cary 50 Probe UV-screw spectrophotometer. Luminescence measurements in the visible at low resolution (spectra, lifetimes, triplet states) were recorded on a Perkin-Elmer LS-50B spectrophotometer at 298K. The spectrometer was equipped with an adaptor for the solid state comprising a liquid nitrogen cooling system, for spectra and measurements of the solid triplet state at 77K.

Quartz cells with a 1 cm optical path were used for measurements at ambient temperature; measurements at 77 K were made with 3 mm diameter quartz capillaries. The singlet state was measured on solutions in methanol and the triplet state was measured on solids at 77K after a delay of 0.2 ms.

In the solid state and in water, the medium resolution excitation and emission spectra and lifetime measurements and quantum yields were made on a Fluorolog FL 3-22spectrometer sold by *Spex-Jobin-Yvon-Horiba* with a double framework excitation monochromator, an iHR320 imager for emission fitted with a turret with two frameworks (blazed at 500 and 1200 lines and blazed at 1000 nm and 600 lines) and a Hamamatsu R928P photomultiplier (range 260 -850 nm). For measurements in the NIR range, the spectrometer is fitted with a second measurement channel comprising a Hamamatsu R5509 monochromator (range 260-1700 nm). Phosphorescent lifetimes are measured by recording the maximum decay of the emission spectrum. Signals are analysed in mono-exponential decay with the OriginLab Origin Pro software and reported values are averages obtained on three independent measurements. Quantum yields of the complexes were determined at ambient temperature by an absolute method and the use of an integration sphere developed at EPFL (Lausanne, Switzerland) and marketed by GMP SA (Renens, Switzerland) and coupled to the Fluorolog FL 3-22 modular spectrofluorimer. Reported values are averages between three different measurements. The absolute quantum yield was calculated according to the following equation:

$$\Phi = \frac{E_c}{L_a - L_c} = \frac{E_c}{L_a \cdot \alpha}$$

and $$\alpha = \frac{L_a - L_c}{L_a}$$

wherein Ec is the emission spectrum in the emission range of the sample (for example if the maximum emission is 600 nm, the range of this spectrum will be 450 to 750 nm), Lc is the emission spectrum of the excitation wavelength of the sample, La is the emission spectrum of the excitation wavelength of the reference (3 mm diameter quartz capillary tubes filled with the solvent used or an inert solid). Emission and excitation spectra were corrected as a function of the intensity of the light source and the spectral emission response.

Example 1

In-Situ Synthesis and NMR Spectra of Complexes [Ln(pytz)$_3$)]$^{3-}$.($^1$NHOct$_3$)$_3$ In Situ Synthesis Protocol.

NMR tubes are prepared at a concentration of $1.5 \times 10^{-2}$ M in the final complex. 5 mL of a $5.28 \times 10^{-2}$ M stock solution of deprotonated H$_2$pytz ligand in MeOD is prepared from 57.18 mg of ligand and 232 µL of trioctylamine. The necessary volumes of stock solution and the quantity of powder Ln triflate (previously titrated, 1 equivalent for 3 equivalents of deprotonated ligand) are then added so that each NMR tube contains 500 µL of a complex solution at a concentration of $10^{-2}$ M. The in situ synthesis method therefore repeats the conventional synthesis without the column purification step.

Complex [Eu(pytz)$_3$)]$^{3-}$.($^+$NHOct$_3$)$_3$

Figure 1:
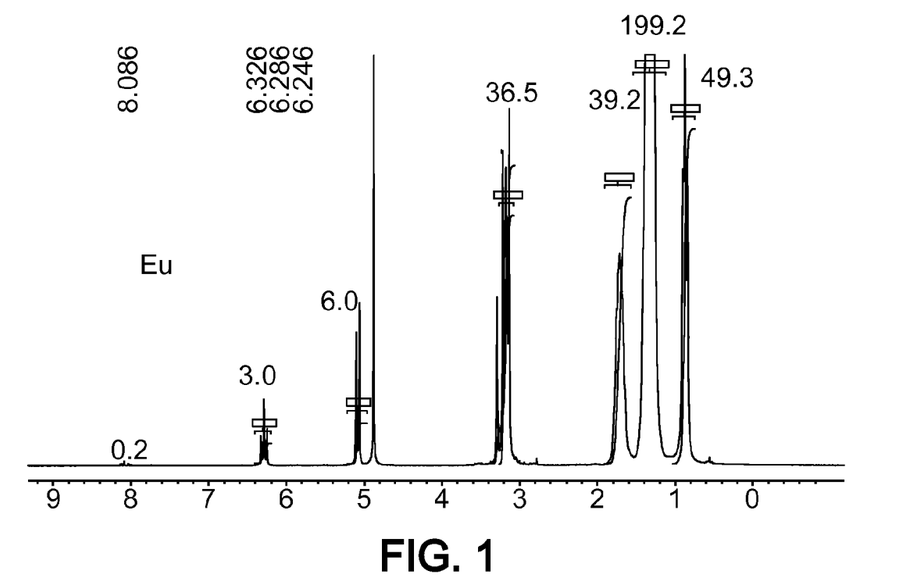
FIG. 1 shows the $^1$H NMR spectrum of the $[Eu(pytz)_3)]^{3-}.(^+NHOct_3)_3$ complex generated in situ in MeOD.

The Eu complex was initially generated in order to compare it with the column isolated complex using a conventional synthesis (see *Dalton Trans.*, 2012, 41, 1268-1277). An analysis of the $^1$H NMR spectrum of the [Eu(pytz)$_3$](NHOct$_3$)$_3$ complex synthesised in situ (FIG. 1) shows that it is consistent with the same complex obtained by conventional synthesis. The $^1$H NMR spectrum clearly shows the presence of a triplet and a doublet counting for 3 and 6 protons at 6.4 and 5.15 ppm respectively in the auto-assembled complex 3:1. The free ligand is present in a proportion of 3% as in the complex isolated by conventional synthesis. Since the complex is generated in situ, peaks corresponding to the three trioctylammonium counter-ions and three trioctylamines used to deprotonate the ligand are observed between 0 and 4 ppm. This experiment clearly confirms the presence of the complex, its D$_3$ symmetry and its stability in solution.

The NMR spectra of complexes generated in solution in situ were made for lanthanides located at the ends of the series, Neodymium (Nd) and Ytterbium (Yb), so as to determine if the complexes actually form in solution regardless of the lanthanide used and if they are stable in solution.

Complex [Nd(pytz)$_3$]$^{3-}$.($^+$NHOct$_3$)$_3$

Figure 2:
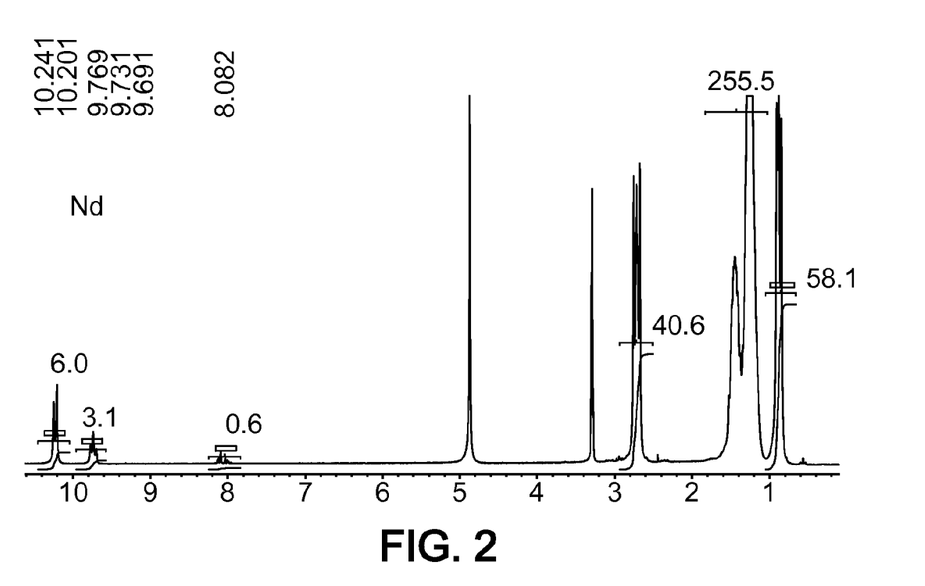
FIG. 2 shows the $^1$H NMR spectrum of the $[Nd(pytz)_3)]^{3-}.(^+NHOct_3)_3$ complex generated in situ in MeOD.

The spectrum for the Nd complex (FIG. 2) clearly shows the presence of signals from the ligand symmetrically complexed by the triplet and the doublet that are centred at 10 ppm, trioctylamine at 6 equivalents and the free ligand at 6%.

Complex [Yb(pytz)$^3$]$^{3-}$.(+NHOct$_3$)$_3$

Figure 3:
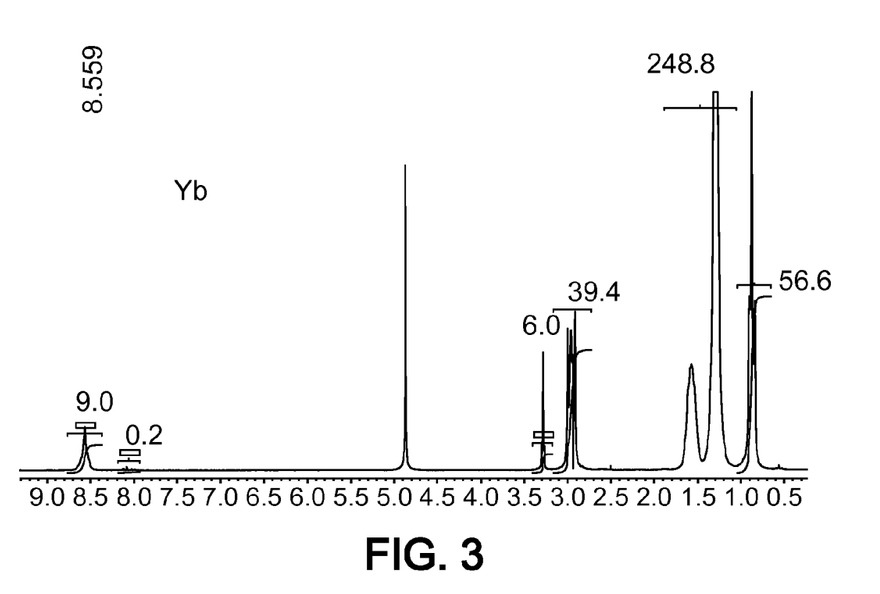
FIG. 3 shows the $^1$H NMR spectrum of the $[Yb(pytz)_3)]^{3-}.(^+NHOct_3)_3$ complex generated in situ in MeOD.

Finally, the spectrum for the Yb complex (FIG. 3) clearly shows the presence of signals from the ligand symmetrically complexed by the triplet and the doublet that are superposed at 8.6 ppm, and trioctylamine at 6 equivalents; the free ligand counts for 3%.

In conclusion, the metallic complexes may be generated in solution in situ while maintaining the coordination of the lanthanide by three deprotonated ligands and three trioctylammonium counter-ions. Furthermore, three trioctylamines are present in solution but do not interfere in complexing. The NMR of the Europium complex isolated on Sephadex LH-20 clearly shows that the three trioctylamines that were used to deprotonate the ligand and in excess can be separated if the pure complex has to be used. This may be reproduced for luminescent complexes with good quantum yield in the visible, Terbium, Samarium and Dysprosium. The small percentage of the free ligand in solution does not interfere in measurements or the stability of complexes because its content is less than 10%.

Example 2

Luminescent Properties of Complexes [Ln(pytz)$_3$]$^{3-}$ ($^+$NHOct$_3$)$_3$

The following procedure is used for preparation of complexes and the study of their photophysical properties in solution: 2 trioctylamine equivalents are added to a suspension of H$_2$pytz ligand in methanol. The solution is stirred for 4 hours after the addition of ⅓ equivalent of lanthanide triflate.

Measurements on this solution are made in 3 mm diameter quartz suprasil capillaries or luminescence cells with a 1 cm optical path. For measurements in the solid state, the solution is evaporated dry and the residue is dried for 2 days under low pressure. The solid obtained is inserted into 3 mm diameter capillaries that are used for the measurement.

FIGS. 4 to 7 show excitation and emission spectra of the different complexes.

The quantum yields and lifetimes in solution and in the solid state are summarised in Table 1 below.

TABLE 1

Lifetimes and absolute quantum yields of lanthanide complexes Ln(pytz)$_3$]$^{3-}$ ($^+$NHOct$_3$)$_3$ in the solid state and in solution in methanol.

| Metal | $\tau_{solid}$/ms | $\tau_{MeOH}$/ms | $\Phi_{solid}$/% | $\Phi_{MeOH}$/% |
|---|---|---|---|---|
| Eu | 3.11 (4) | 3.38 (2) | 61.1 (3) | 29.1 (2) |
| Tb | 1.54 (2) | 2.28 (3) | 64.5 (11) | 70.2 (3) |
| Dy | 0.07 (1) | 0.06 (2) | 6.6 (3) | 6.2 (2) |
| Sm | 0.11 (1) | 0.10 (5) | 1.5 (4) | 1.4 (2) |
| Ho | — | — | 0.010 (4) | 0.010 (3) |
| Pr | — | — | 0.040 (5) | 0.010 (7) |
| Tm | — | — | 0.060 (4) | 0.040 (4) |
| Nd | — | — | 0.21 (1) | 0.18 (4) |
| Yb | — | — | 0.35 (4) | 0.37 (8) |

The emission lifetime of the Europium complex measured on the maximum of the $^7$F$_2$ transition under excitation of the ligand at 303 and 322 nm is adjusted mono-exponentially in both the solid state and in solution. This lifetime corresponds to 3.11 ms in the solid state and 3.38 ms in solution in methanol. These results agree well with the absence of water or methanol solvent molecules in the first coordination sphere. The absolute quantum yield is 61.1% in the solid state, one of the highest values reported in the literature (Kottas, *Eur J Inorg Chem*, 2007, 3465) with a maximum for a tris pyridine-bis(oxazoline) europium complex at 76% in acetonitrile (Bettencourt-Dias, *J. Am. Chem. Soc.*, 2007, 129, 15436).

The studied lanthanide complexes are luminescent in different wavelength ranges. They may be separated into three major groups. The first including Europium, Terbium, Dysprosium, Samarium and Thulium that are luminescent in the visible. The second group includes Praseodymium and Holmium that have two luminescence ranges in the Visible and in the Infrared. The third group includes Neodymium and Ytterbium that are luminescent in the Infrared.

Thus, nine complexes are given as examples with dissimilar emission bands, two of which have two different emission zones in the visible and infrared. This allows a large quantity of colour codes simply by mixing different complexes.

Example 3

Figure 4:
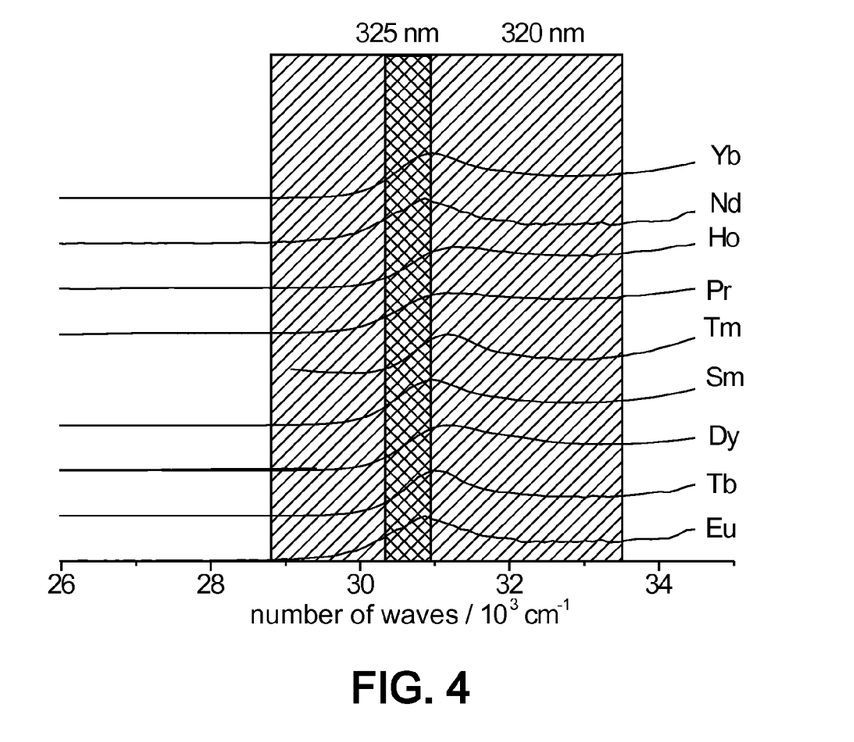
FIG. 4 shows excitation spectrum of lanthanide complexes $[Ln(pytz)_3)]^{3-}.(^+NHOct_3)_3$ in methanol at 25° C. Analysis at the maximum of the most intense transition.

Excitation and Emission Spectra of Complexes [Ln(pytz)$_3$]$^{3-}$.($^+$NHOct$_3$)$_3$ The excitation spectrum of lanthanide complexes [Ln(pytz)$_3$]$^{3-}$.(+NHOct$_3$)$_3$ in methanol at 25° C. is shown in FIG. 4. It clearly shows that the excitation spectra of complexes are practically identical. Regardless of which lanthanide cation is used, complexes may be excited at an identical wavelength so that many complexes can be sensitised by applying a single UV wavelength. This wavelength can vary from 270 to 330 nm while preserving the luminescence of complexes and unique transitions of each lanthanide.

Figure 5:
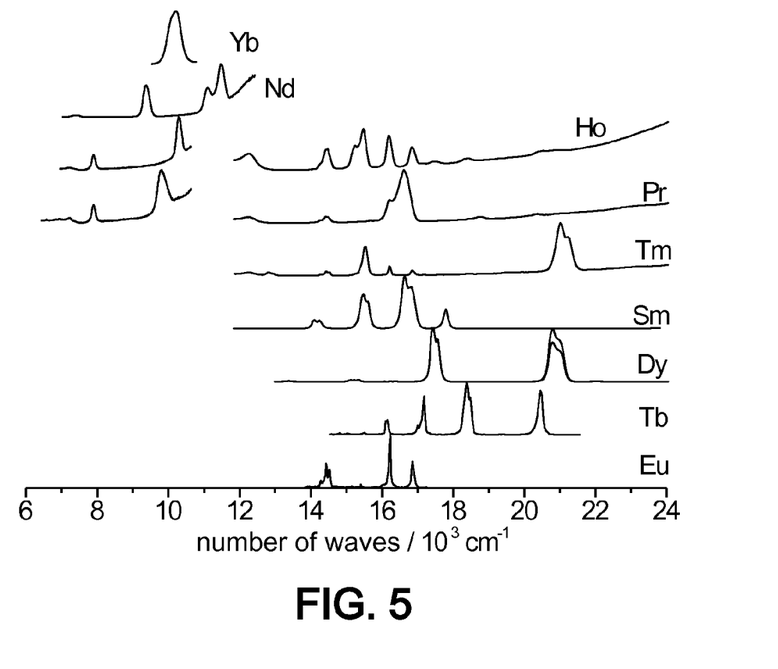
FIG. 5 shows the emission spectrum of lanthanide complexes $[Ln(pytz)_3)]^{3-}.(^+NHOct_3)_3$ in methanol at 25° C. Excitation at 322 nm.

FIG. 5 shows emission spectra of lanthanide complexes prepared from stock solutions in methanol. Characteristic transitions of the different lanthanide ions are observed on wavelengths varying from 400 to 1600 nm, and may be isolated or overlap depending on the zone. The spectra are unchanged regardless of the excitation wavelength between 270 and 330 nm, which is an essential characteristic of lanthanide complexes according to the invention.

Figure 6:
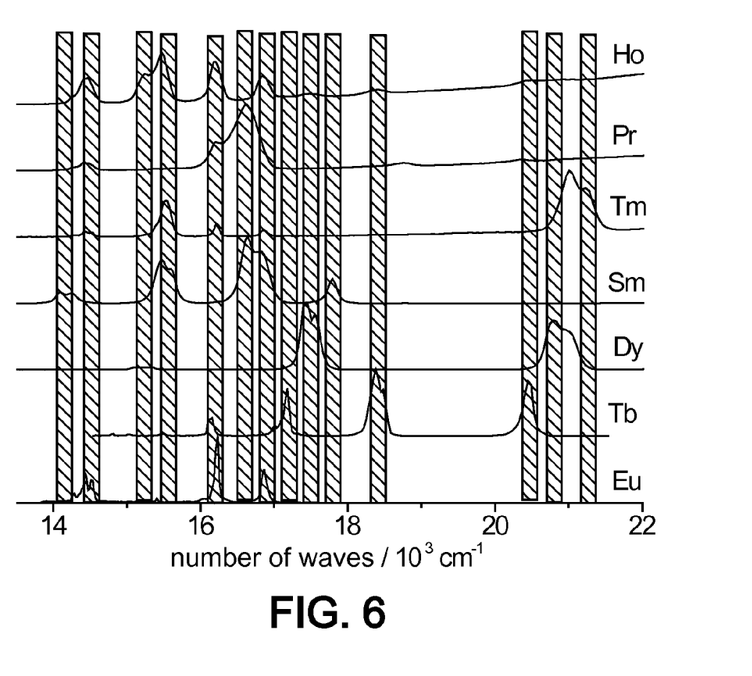
FIG. 6 shows a zoom in the visible range of the emission spectrum of lanthanide complexes $[Ln(pytz)_3)]^{3-}.(+NHOct_3)_3$ in methanol at 25° C. Excitation at 322 nm. The cross-hatched zones show emission zones that can be used and lanthanides that can be used.

A zoom on the Visible zone with the associated lanthanide cations is shown in FIG. 6. Cross-hatched bands show characteristic zones that can be used in the fabrication of optical codes. Each lanthanide ion emits in a different zone and may be associated with one or several other lanthanide ions. An optical code may be formed from two or more lanthanide complexes. Furthermore, the code can then be re-multiplied by relative intensities since the quantum yields are different and the transitions of each lanthanide have a different intensity.

Example 4

Figure 7:
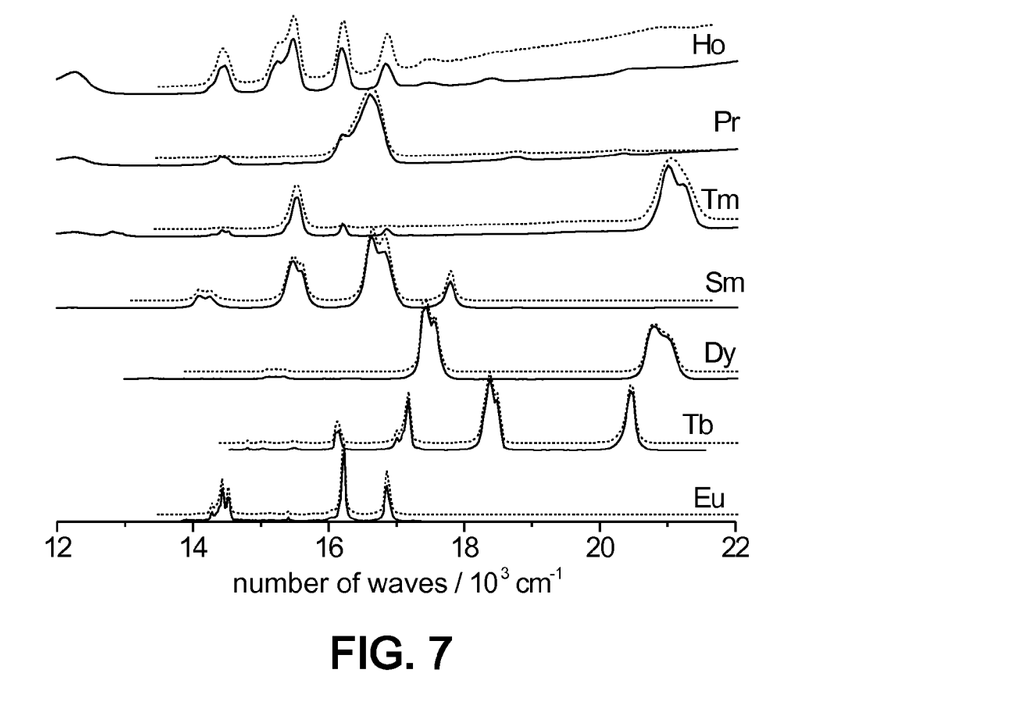
FIG. 7 shows the emission spectrum of lanthanide complexes $[Ln(pytz)_3)]^{3-}.(+NHOct_3)_3$ in methanol (black dashed lines) and in the solid state (black) at 25° C. Excitation at 322 nm.

Emission Spectra of [Ln(pytz)$_3$]$^{3-}$.($^+$NHOct$_3$)$_3$ Complexes in the Solid State and in Solution in Methanol FIG. 7 shows emission spectra of lanthanide complexes in solution and in the solid state. These spectra clearly show that transitions remain identical for relative intensity and for centering in wavelength of their maxima, regardless of the formulation. The medium wherein the complex is inserted does not influence the quality of emission spectra that are superposed perfectly and do not cause any displacement of the wavelengths of successive transitions.

Example 5

Four-Colour Optical Code

A four-colour code was produced composed of a mix of four complexes [Sm(pytz)$_3$]$^{3-}$($^+$NHOct$_3$)$_3$; [Dy(pytz)$_3$]$^{3-}$.($^+$NHOct$_3$)$_3$; [Tb(pytz)$_3$]$^{3-}$.($^+$NHOct$_3$)$_3$; [Eu(pytz)$_3$]$^{3-}$.($^+$NHOct$_3$)$_3$. Their quantum yields in solution in methanol are 1.4, 6.2, 70 and 29% respectively. Therefore, in order to obtain a solution with a maximum intensity of 1 starting from stock solutions with identical concentration (for example 0.01 M), as a first approximation the corresponding volumes of each of the stock solutions have to be in the proportion of 50, 11.4, 2.4 and 1 (sample 1). Quantities may also be adjusted depending on the maximum intensity of the complexes (sample 2). The composition of the two samples is given in Table 2.

TABLE 2

Volume ratios used and volumes of stock solutions of Ln(pytz)$_3$](NHOct$_3$)$_3$ at 10$^{-2}$ M in methanol added to prepare 500 µL of solution (final concentration Ech. 1 = 8.9. × 10$^{-3}$ M; Ech. 2 = 4.4 × 10$^{-3}$ M)

| | Sample 1 | | Sample 2 | |
|---|---|---|---|---|
| Ln | Ratio | Volume (µL) | Ratio | Volume (µL) |
| Eu | 2.7 | 27 | 5.4 | 54 |
| Tb | 1 | 10 | 1 | 1 |
| Dy | 11.8 | 118 | 8.7 | 87 |
| Sm | 28.4 | 284 | 13.8 | 138 |
| MeOH | | 61 | | 280 |

Figure 8:
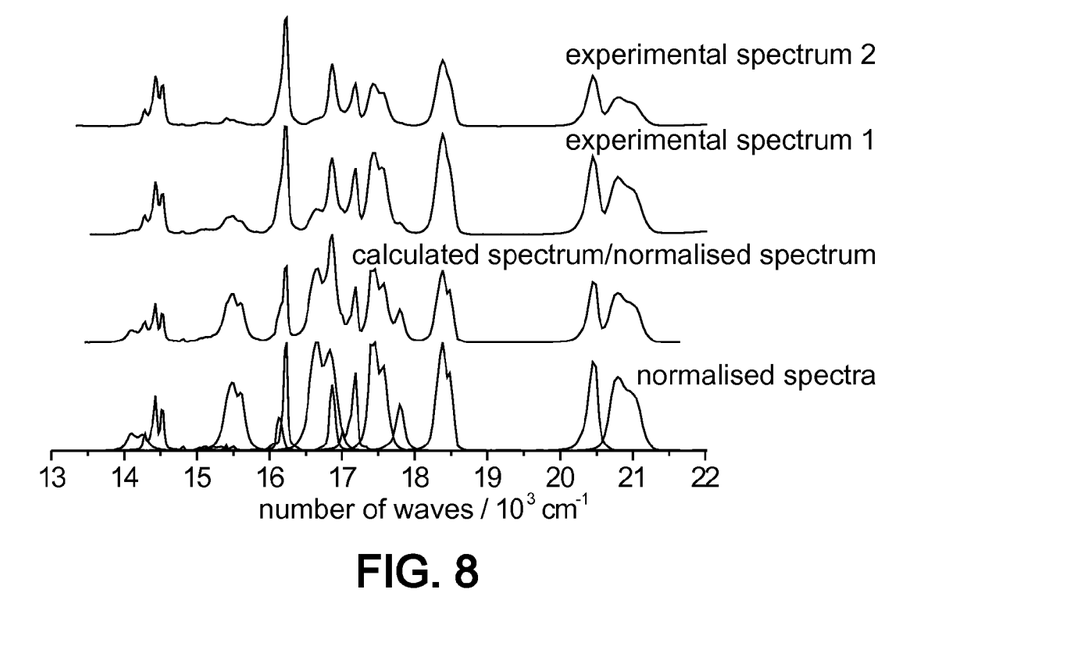
FIG. 8 shows normalised experimental spectra starting from a mix of complexes of $[Sm(pytz)_3)]^{3-}.(+NHOct_3)_3$, $[Dy(pytz)_3)]^{3-}.(+NHOct_3)_3$, $[Tb(pytz)_3)]^{3-}.(+NHOct_3)_3$ and $[Eu(pytz)_3)]^{3-}.(+NHOct_3)_3$ in proportions 28.4, 11.8, 1, 2.7 and 13.8, 8.7, 1 and 5.4 for experimental spectra 1 and 2 respectively, and theoretical spectra for mixes calculated from proportions 50, 11.4, 1 and 2.4.

The emission spectra (excitation at 322 nm) obtained are shown in FIG. 8. This figure shows from bottom to top, superposition of theoretical normalised emission spectra for each of the four lanthanide complexes used, the recalculated spectrum that should be obtained for ratios in complexes of Sm, Dy, Eu and Tb equal to 50, 11.4, 2.4 and 1 respectively, and measured spectra of the two mixes of four stock solutions of lanthanide complexes with identical concentrations (samples 1 and 2). The experimental spectra for the two samples accurately reproduce the theoretical spectrum.

Emission spectra from sample 1 obtained by varying the excitation wavelength are identical concerning emitted wavelengths but the intensity varies as a function of the excitation wavelength. Maxima are one excitation wavelength of 305 nm and correspond to maximum absorption of all lanthanide complexes.

Figure 9A:
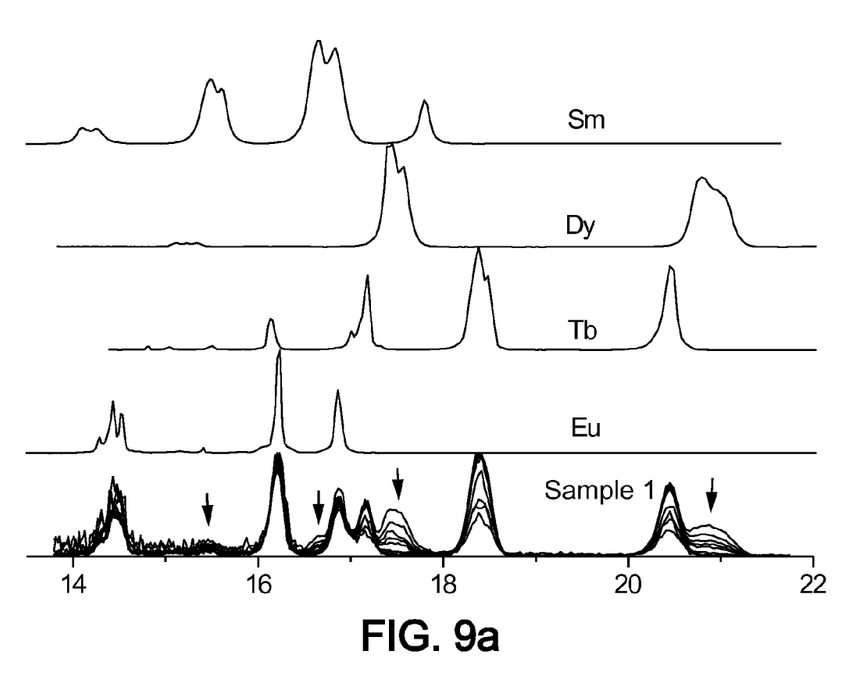
FIG. 9a shows emission spectra of sample 1 after application of a delay varying from 0.01 to 15 ms between the flash of the excitation lamp and the measurement of the emitted luminescence signal; resolved time spectrometry. In particular.
Figure 9B:
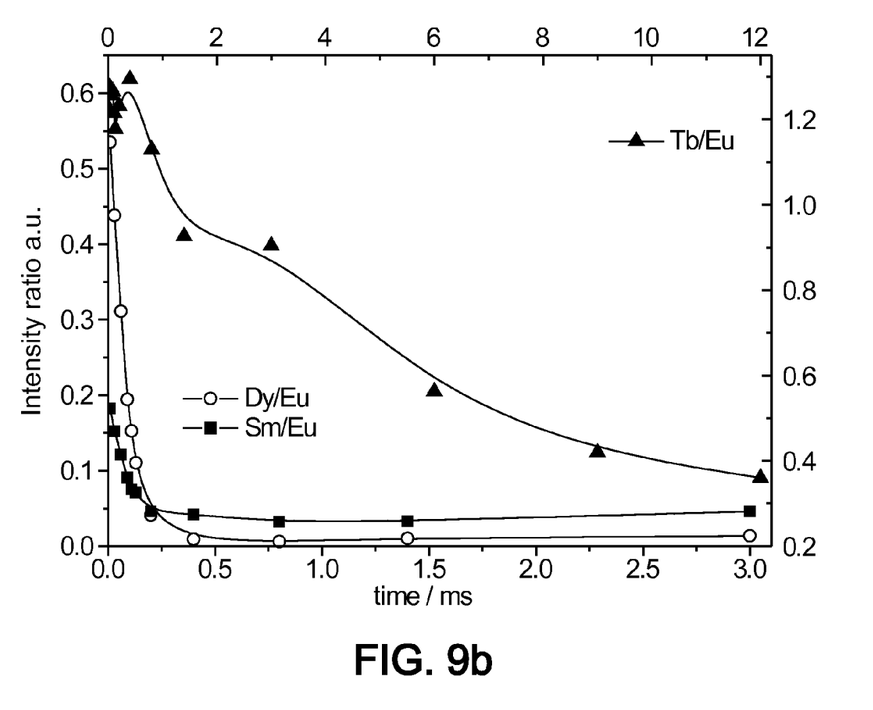
FIG. 9b shows the variation of the intensity ratios of four complexes of sample 1 after application of a delay of 0.01 to 15 milliseconds.

The resolved time emission spectra of sample 1 are shown in FIGS. 9a and 9b. These figures show the variation of luminescence as a function of application of a delay of 0.01 to 15 milliseconds in sample 1. FIG. 9a also shows the emission spectra obtained by resolved time measurement of the four Sm, Dy, Tb and Eu complexes, from top to bottom. None of the bands (shown by arrows) corresponding to the Sm and Dy transitions appear in the spectrum for sample 1. Lifetimes of the excited states of these two complexes are 0.01 and 0.06 ms respectively, while the lifetimes of Tb and Eu are 2.28 and 3.38 ms respectively. FIG. 9b very clearly shows the possibility of implementing an optical code varying in time, detected by resolved time spectrometry, and consequently is very complex to identify and reproduce. A luminescence measurement after a delay time of 0.5 milliseconds shows the disappearance of bands corresponding to Dy and Sm, unlike the case of a continuous measurement for which these bands will be at the same level as Tb and Eu.

The invention claimed is:
1. A method of optical marking of products comprising:
a step of applying a composition comprising at least one lanthanide complex and a vehicle on at least part of a surface or a product; or a step of incorporating a composition comprising at least one lanthanide complex and a vehicle into at least part of a product, the at least one lanthanide complex having a Formula I:

$$[Ln(L)_3]^{3-}.Cat \qquad (I)$$

wherein:

the at least one lanthanide complex has a balanced charge;

Ln is a lanthanide;

Cat is a cation selected to balance the charge of the complex and is selected from $Na^{3O}$, $K^+$, $Cr^{3+}$, $Fe^{3+}$, $Fe^{2+}$, $Co^{2+}$, $Cu^{2+}$, $Mo^{6+}$, $Ru^{4+}$, $Ir^{4+}$, $Pt^{4+}$, $^+NHR^aR^bR^c$ wherein $R^a$, $R^b$ and $R^c$ may be identical or different and are independently from one another, $C_2$ to $C_{15}$ alkyl optionally substituted by one or more substituents selected from $C_2$ to $C_3$ alkenyl, aryl and heteroaryl, and $^+PR^dR^eR^fR^g$ wherein $R^d$, $R^e$, $R^f$ and $R^g$ may be identical or different and are independently selected from $C_1$ to $C_5$ alkyl and phenyl; and L is a ligand of formula II:

wherein, $R^1$ is selected from a hydrogen atom,

-continued wherein
$R^2$ is $C_1$ to $C_3$ alkyl;
$R^3$ is a hydrogen atom or $C_1$ to $C_3$ alkyl;
$Ar^1$ is 5- or 6-membered phenyl or heteroaryl; and
the dashed lines indicate the point of attachment to the pyridine ring.

2. The method of claim 1, wherein Ln is selected from the group consisting of praseodymium, neodymium, samarium, europium, terbium, dysprosium, holmium, thulium and ytterbium.

3. The method of claim 1, wherein Cat is $^+NHR^aR^bR^c$ wherein $R^a$, $R^b$ and $R^c$ are identical.

4. The method of claim 3, wherein $R^a$, $R^b$ and $R^c$ all three are selected from ethyl and n-octyl.

5. The method of claim 1, wherein $R^1$ is a hydrogen atom.

6. The method of claim 1, wherein the composition comprises at least two lanthanide complexes according to Formula I, wherein the L and Cat groups are identical for each complex, but differ from each other only by the lanthanide Ln.

7. The method of claim 1, wherein the composition comprises four lanthanide complexes of Formulae V, VI, VII and VIII, $[Sm(L)_3)]^{3-}.(^+NHR^aR^bR^c)_3$ (V);

$[Dy(L)_3)]^{3-}.(^+NHR^aR^bR^c)_3$ (VI);

$[Tb(L)_3)]^{3-}.(^+NHR^aR^bR^c)_3$ (VII);

$[Eu(L)_3)]^{3-}.(^+NHR^aR^bR^c)_3$ (III);

wherein
$R^a$, $R^b$ and $R^c$ are selected from ethyl and n-octyl;
L is the ligand of Formula II wherein $R^f$ is a hydrogen atom.

* * * * *